United States Patent
Jin et al.

(10) Patent No.: US 9,642,587 B2
(45) Date of Patent: May 9, 2017

(54) HIGH-VOLTAGE MEDICAL POWER SUPPLY DEVICE AND CONTROLLING METHOD THEREOF

(71) Applicant: DELTA ELECTRONICS, INC., Taoyuan (CN)

(72) Inventors: Hongyuan Jin, Taoyuan (CN); Jun Liu, Taoyuan (CN); Dezhi Jiao, Taoyuan (CN)

(73) Assignee: Delta Electronics, Inc., Taoyuan (TW)

( * ) Notice: Subject to any disclaimer, the term of this patent is extended or adjusted under 35 U.S.C. 154(b) by 0 days.

(21) Appl. No.: 15/000,115

(22) Filed: Jan. 19, 2016

(65) Prior Publication Data

US 2016/0211756 A1    Jul. 21, 2016

(30) Foreign Application Priority Data

Jan. 19, 2015 (CN) .......................... 2015 1 0025961

(51) Int. Cl.
*H02M 3/156* (2006.01)
*A61B 6/00* (2006.01)
(Continued)

(52) U.S. Cl.
CPC ............. *A61B 6/54* (2013.01); *H02M 3/3353* (2013.01); *H02M 3/3378* (2013.01);
(Continued)

(58) Field of Classification Search
CPC ...... H02M 3/155; H02M 3/156; H02M 3/158; H02M 3/335; H02M 3/33507;
(Continued)

(56) References Cited

U.S. PATENT DOCUMENTS 4,741,010 A * 4/1988 Hino .................. H05G 1/32
363/17
5,265,146 A * 11/1993 Wirth .................. H05G 1/66
378/101
(Continued)

FOREIGN PATENT DOCUMENTS

CN      101399493 A    4/2009
CN      101699740 B    8/2011
(Continued)

OTHER PUBLICATIONS

1st Office Action issued on Mar 20, 2017 by the TW Office.

*Primary Examiner* — Matthew Nguyen
(74) *Attorney, Agent, or Firm* — Yunling Ren

(57) ABSTRACT

A power supply device includes a power supply module, a high voltage conversion module and a control module. The high voltage conversion module includes a first high-voltage output module and a second high-voltage output module both connected to the power supply module. The control module is connected to the first high-voltage output module and the second high-voltage output module to respectively sample a first output voltage of the first high-voltage output module and a second output voltage of the second high-voltage output module and generate a power control signal, a first control signal and a second control signal respectively used to control the power supply module, the first high-voltage output module and the second high-voltage output module. There is a phase difference between the first control signal and the second control signal to interleaving control the first high-voltage output module and the second high-voltage output module.

19 Claims, 16 Drawing Sheets

(51) Int. Cl.
*H02M 3/335* (2006.01)
*H02M 3/337* (2006.01)
*H02M 1/00* (2006.01)

(52) U.S. Cl.
CPC ...... *H02M 3/156* (2013.01); *H02M 2001/007* (2013.01); *H02M 2001/0058* (2013.01); *Y02B 70/1491* (2013.01)

(58) Field of Classification Search
CPC ........... H02M 3/3353; H02M 3/33569; H02M 3/337; H02M 3/3378; H02M 2001/007; H02M 2001/0058; A61B 6/00; A61B 6/54; H05G 1/30; H05G 1/32; H05G 1/48
See application file for complete search history.

(56) References Cited

U.S. PATENT DOCUMENTS

| | | | |
|---|---|---|---|
| 7,554,825 B2 * | 6/2009 | Chuang | H02M 3/335 307/51 |
| 2012/0163051 A1 | 6/2012 | Vogman | |
| 2014/0354057 A1 | 12/2014 | Chen et al. | |
| 2016/0105193 A1 * | 4/2016 | Oshima | H03M 1/403 341/163 |

FOREIGN PATENT DOCUMENTS

| | | |
|---|---|---|
| CN | 102545596 A | 7/2012 |
| TW | I397249 B | 5/2013 |

* cited by examiner

HIGH-VOLTAGE MEDICAL POWER SUPPLY DEVICE AND CONTROLLING METHOD THEREOF

CROSS-REFERENCE TO RELATED APPLICATIONS

This application claims priority under 35 U.S.C. §119 to Chinese Patent Application No. 201510025961.2, filed on Jan. 19, 2015, the entire contents of which are incorporated herein by reference.

TECHNICAL FIELD

The present disclosure relates to the field of a power supply device, and more particularly, to a high-voltage medical power supply device and a controlling method thereof.

BACKGROUND

X-ray apparatuses are widely used for healthcare and the research of Basic Sciences, such as medicine, life sciences, Nondestructive Testing. A high-voltage medical power supply device is the core of the X-ray apparatus, which provides high voltages to generate X-Ray. The high-voltage medical power supply device have wide output voltage ranges, so that the X-ray apparatuses used in diagnosis can meet the imaging requirements of different people and different parts of the body.

It is essential for the X-ray apparatus to decrease its size and weight. One way is increasing the operation frequency of the high-voltage medical power supply device. The operation frequency can be observed on the high voltage output. In diagnosis X-ray apparatus, the high-voltage medical power supply devices have a positive output voltage +HV and a negative output voltage −HV, and the positive output voltage +HV and the negative output voltage −HV are superposed to obtain a high output voltage Vo. By this way, the ripple of the output voltage Vo will be added. FIG. 1 shows ripple diagrams of +HV, −HV and Vo. As illustrated in FIG. 1, the output voltage Vo has high ripple, the peak of which is approximately twice as much as that of the positive output voltage +HV or negative output voltage −HV. To the X-ray apparatus, the output voltage with high ripple will decrease the imaging precision and the image quality. So reducing the ripple of the output voltage provided by the high-voltage medical power supply device and improving the imaging precision are urgent issues to be solved in the X-ray apparatus.

SUMMARY OF THE INVENTION

A high-voltage medical power supply device, including: a power supply module, a high voltage conversion module comprising a first high-voltage output module and a second high-voltage output module that are both electrically connected to an output terminal of the power supply module; and a control module electrically connected to an output terminal of the first high-voltage output module and an output terminal of the second high-voltage output module to respectively sample a first output voltage of the first high-voltage output module and a second output voltage of the second high-voltage output module, and according to the first output voltage and the second output voltage obtained from sampling, the control module outputting a power control signal, a first control signal and a second control signal, respectively used to control the power supply module, the first high-voltage output module and the second high-voltage output module; wherein there is a phase difference between the first control signal and the second control signal to interleaving control the first high-voltage output module and the second high-voltage output module.

In another aspect, the present disclosure also provides a method of controlling a high-voltage medical power supply device, which includes: a power supply module outputting a first power supply voltage and a second power supply voltage; a first high-voltage output module and a second high-voltage output module of a high voltage conversion module respectively receiving the first power supply voltage and the second power supply voltage and correspondingly outputting a first output voltage and a second output voltage; a control module sampling the first output voltage and the second output voltage and generating a power control signal, a first control signal and a second control signal according to sampling signals of the first output voltage and the second output voltage; and the first output module receiving the first control signal, and the second output module receiving the second control signal, wherein, there is a phase difference between the first control signal and the second control signal.

DETAILED DESCRIPTION

Figure 1:
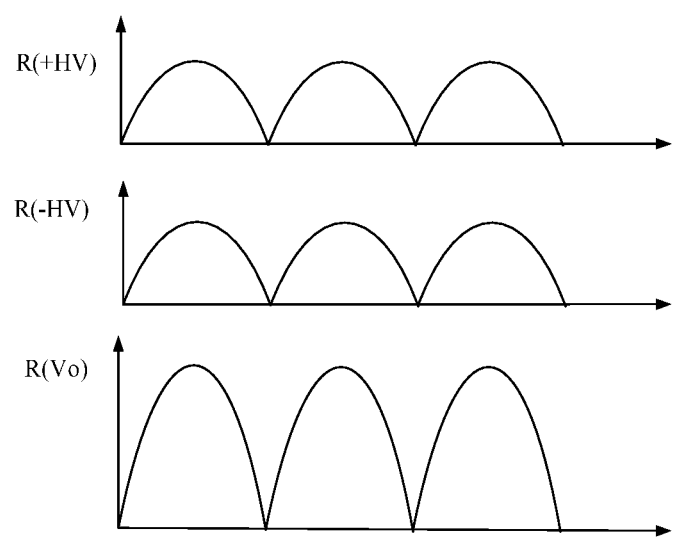
FIG. 1 is a schematic view showing the ripple of the output voltage of the power supply device.

Detailed description of the present disclosure will be made with reference to drawings and embodiments. It shall be appreciated that the embodiments described herein are for the purposes of illustration but not to limit the present disclosure. In addition, it shall be noted that only the parts related to the present disclosure but not all the structures are shown in the drawings for the convenience of description.

Figure 2:
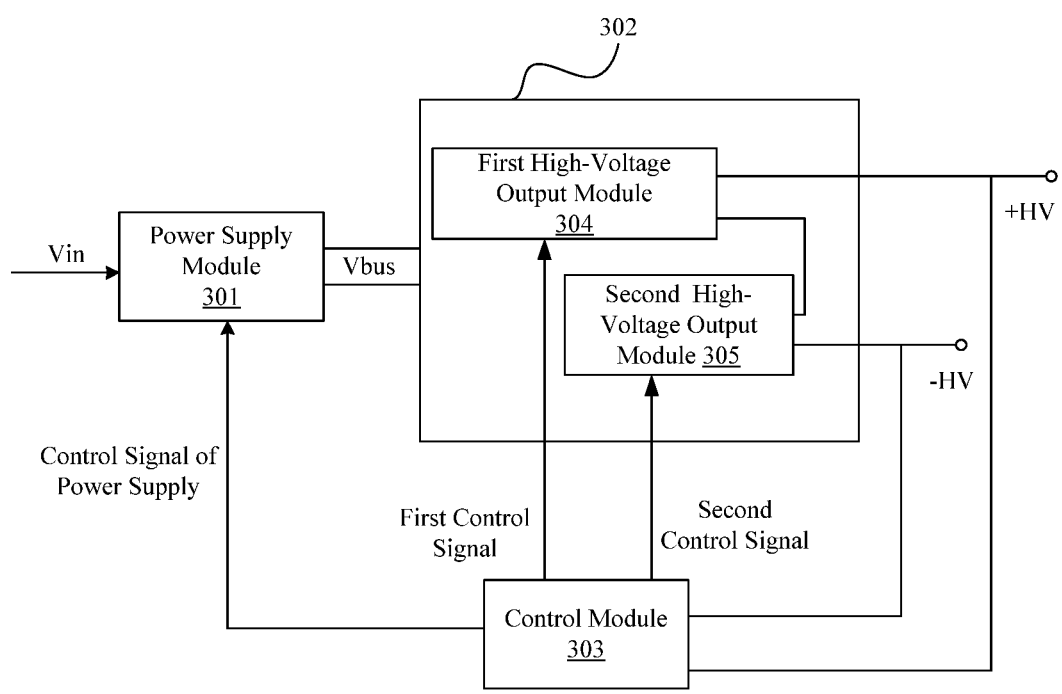
FIG. 2 shows a structural block diagram according to the present disclosure.

The present disclosure provides a high-voltage medical power supply device, the structural diagram of which is shown in FIG. 2. The high-voltage medical power supply device includes a power supply module 301, a high voltage conversion module 302 and a control module 303. The high voltage conversion module includes a first high-voltage output module 304 and a second high-voltage output module 305. The first high-voltage output module 304 and the second high-voltage output module 305 are electrically connected to the output terminals of the power supply module 301. The control module 303 is electrically connected with the output terminals of the first high-voltage output module 304 and the second high-voltage output module 305 to sample the first output voltage of the first high-voltage output module and the second high-voltage output voltage of the second output module respectively. According to the sample signals of the first output voltage and the second output voltage, the control module generates a power control signal to control the power supply module 301 and a first control signal and a second control signal to interleaving control the first high-voltage output module 304 and the second high-voltage output module 305. Wherein, there is a phase difference between the first control signal and the second control signal.

The output terminals of the first output module 304 are coupled with the output terminals of the second output module 305 in series. As described above, the overall structure of the high-voltage medical power supply device of the present disclosure is illustrated in conjunction with FIG. 2, and the specific structure of the high-voltage medical power supply device and the advantage compared with the prior art will be described in detail with reference to the specific embodiments.

Figure 3:
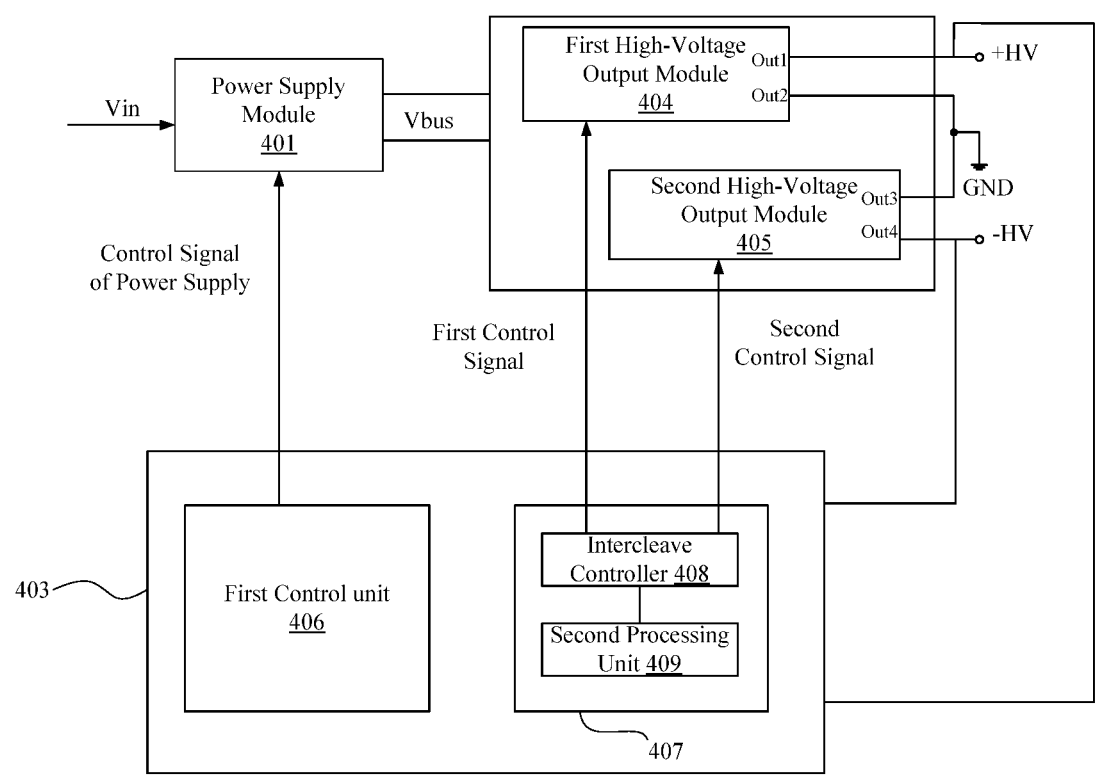
FIG. 3 shows a circuit diagram of the high-voltage medical power supply device according to the first embodiment of the present disclosure.

FIG. 3 shows a circuit diagram of a high-voltage medical power supply device according to the first embodiment of the present disclosure. The high-voltage medical power supply device includes a power supply module 401, a high voltage conversion module and a control module 403. The power supply module 401 receives an input voltage Vin, and then outputs a power supply voltage Vbus. Preferably, the power supply voltage is DC voltage. The high voltage conversion module includes a first high-voltage output module 404 and a second high-voltage output module 405. Wherein the first high-voltage output module 404 and second high-voltage output module 405 are both electrically connected with the output terminals of the power supply module 401 to receive the power supply voltage Vbus and respectively output a first output voltage and a second output voltage. The first output voltage is a positive output voltage +HV, and the second output voltage is a negative output voltage −HV The first high-voltage output module 404 has the first output terminal Out1 and the second output terminal Out2, and the second high-voltage output module 405 has the third output terminal Out3 and the fourth output terminal Out4. The second output terminal Out2 and the third output terminal Out3 are connected and grounded so that the output terminals of the first high-voltage output module 404 are coupled with the output terminals of the second high-voltage output module 405 in series. And the series connection of the positive output voltage +HV and the negative output voltage −HV can be realized to generate a high output voltage.

In FIG. 3, the control module 403 includes the first control unit 406 and the second control unit 407. The control module 403 is connected with the first output terminal Out1 of the first high-voltage output module 404 and the fourth output terminal Out4 of the second high-voltage output module 405 to sample the positive output voltage +HV and the negative output voltage −HV. The first control unit and the second control unit receive the sampling results. According to the sampling result, the first control unit 406 outputs the power supply control signal to control the power supply module 401. The second control unit 407 includes an interleaving controller 408 and a second processing unit 409. According to the sampling results, the second control unit 407 outputs the first control signal and the second control signal to respectively control the first high-voltage output module 404 and second high-voltage output module 405 which turn on and off in interleaving mode. There is a phase difference between the first control signal and the second control signal, and preferably the phase difference is 180°.

Figure 4:
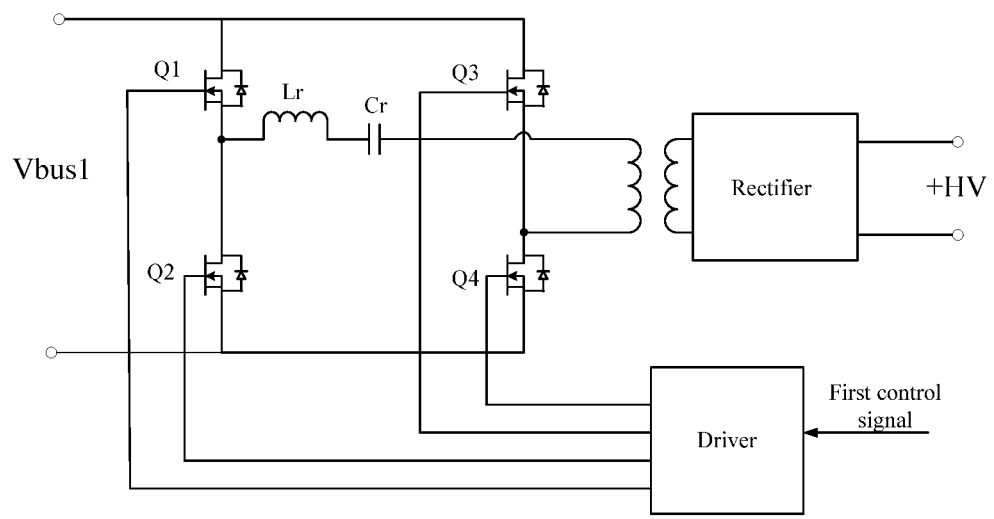
FIG. 4 is a specific circuit diagram of the first high-voltage output module in FIG. 3.

FIG. 4 is a specific circuit diagram of the first high-voltage output module in FIG. 3, which is a series resonance full-bridge DC/DC converter. The series resonance full-bridge DC/DC converter receives the power supply voltage Vbus of the power supply module 401 and outputs the required positive output voltage +HV. Similarly, the second high-voltage output module 405 may also use the series resonance converter shown in FIG. 4. However, it is noted that the first high-voltage output module 404 and the second high-voltage output module 405 can use other resonant converters. FIG. 4 schematically illustrates the structures, which is not to limit and explanations are omitted here.

The controlling method of the high-voltage medical power supply device according to the present embodiment will be described as follows. The method includes the following steps. The input voltage Vin is converted to the power supply voltage Vbus by the power supply module 401. The first high-voltage output module 404 and the second high-voltage output module 405 receive the Vbus and respectively output the positive output voltage +HV and the negative output voltage −HV. The control module 403 samples the positive output voltage +HV and the negative output voltage −HV. And according to the sampling results, the first control unit 406 outputs the power control signal to control the power supply module 401 and the second control unit 407 outputs the first control signal and the second control signal to interleaved control the first high-voltage output module 404 and second high-voltage output module 405.

Figure 5:
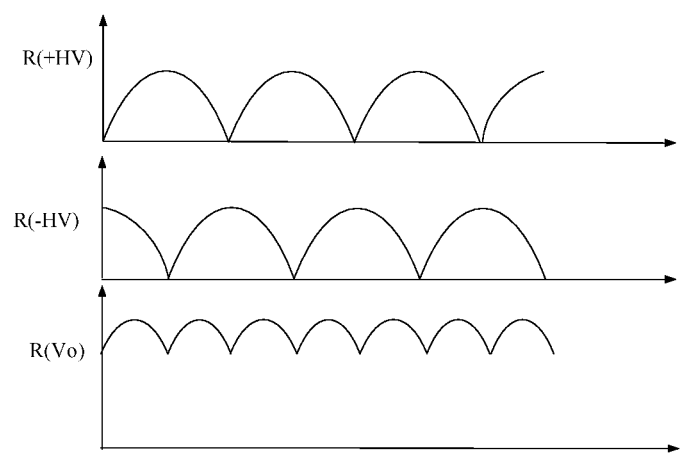
FIG. 5 is a schematic view showing the ripple of the output voltage of the high-voltage medical power supply device shown in FIG. 3.

FIG. 5 is a ripple diagram of the output voltage of the high-voltage medical power supply device shown in FIG. 3. In FIG. 5, R (+HV) denotes the ripple of the positive output voltage, R (−HV) denotes the ripple of the negative output voltage, and R (Vo) denotes the ripple of the high output voltage Vo. As illustrated in FIG. 5, there is a 90° phase difference between the R (+HV) and the R (−HV). As a result, the ripple of the output voltage R (Vo) is reduced greatly compared with the ripple of the output voltage shown in FIG. 1, and the peak of the ripple of the output voltage reduces to be below a quarter of the peak of the ripple of the output voltage shown in FIG. 1.

The high voltage conversion module of the high-voltage medical power supply device of the present disclosure includes the first high-voltage output module and the second high-voltage output module. The output terminals of the two high-voltage output modules are connected in series to output the required high voltage. The interleaving controller controls the two high-voltage output modules to be interleaving conduction, so that the ripple of the output voltage is reduced greatly, the peak of the ripple of the output voltage is less than a quarter of that of the ripple of the output voltage in the prior art. The imaging precision and image quality of the X-ray apparatus which uses the high-voltage medical power supply device of the present embodiment can be improved.

Figure 6:
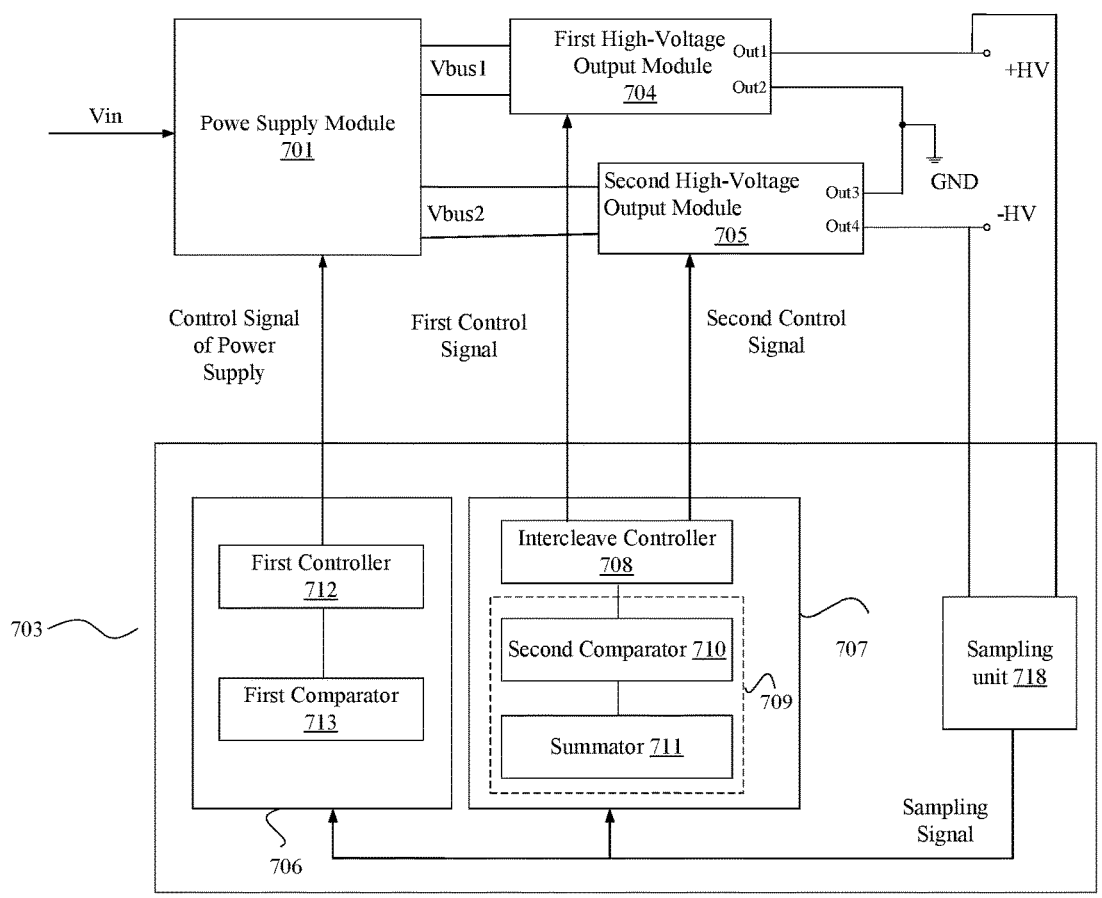
FIG. 6 shows a circuit diagram of the high-voltage medical power supply device according to the second embodiment of the present disclosure.

FIG. 6 shows the circuit diagram of the high-voltage medical power supply device according to the second embodiment of the present disclosure. Comparing with the first embodiment, the present embodiment further describes that the power supply module can output two independent power supply voltages. As illustrated in FIG. 6, the power supply module 701 receives the input voltage Vin and outputs two power supply voltages Vbus1 and Vbus2. Specifically, the first high-voltage output module 704 and the second high-voltage output module 705 are both electrically connected to the output terminals of the power supply module 701. And the first high-voltage output module 704 receives the power supply voltage Vbus1, and the second high-voltage output module 705 receives the other power supply voltage Vbus2. In present embodiment, the first high-voltage output module and the second high-voltage output module have independent power inputs.

In FIG. 6, the control module 703 includes the first control unit 706, the second control unit 707 and the sampling unit 718. The sampling unit 718 is connected with the first output terminal Out1 and the fourth output terminal Out4 to sample the positive output voltage +HV and the negative output voltage −HV. And the sampling unit transfers the sampling results to the first control unit 706 and the second control unit 707.

Further, the first control unit 706 includes the first comparator 713 and the first controller 712 that are connected with each other. The first comparator 713 is connected with the sampling unit 718 to receive the sampling signals corresponding with the positive output voltage +HV and the negative output voltage −HV. The first comparator 713 compares the absolute values of two sampling signals and outputs the first processing signal when the absolute values of two sampling signals are not equal. The first controller 712 is electrically connected with the first comparator 713 to receive the first processing signal, and output the power control signal to control the power supply module 701 according to the first processing signal. And according to the power control signal, the power supply module 701 adjusts at least one of the power supply voltages Vbus1 and Vbus2 to make the absolute values of the positive output voltage +HV and the negative output voltage −HV approximately equal. Specially, if the absolute value of the positive output voltage +HV is larger than that of the negative output voltage −HV, the first comparator 713 outputs the first processing signal. The first controller 712 controls the power supply module 701 to reduce Vbus1 or increase Vbus2, or reduce Vbus1 while increase Vbus2 according to the first processing signal. Similarly, if the absolute value of the positive output voltage +HV is smaller than that of the negative output voltage −HV, the first comparator 713 outputs the first processing signal. The first controller 712 controls the power supply module 701 to increase Vbus1 or reduce Vbus2, or increase Vbus1 while reduce Vbus2 according to the first processing signal.

The second control unit 707 includes the second processing unit 709 and the interleaving controller 708 that are connected with each other. The second processing unit includes the summator 711 and the second comparator 710. The summator 711 is electrically connected to the sampling unit 718 to receive the sampling signals corresponding with the positive output voltage +HV and the negative output voltage −HV and sum the absolute values of two sampling signals to get the sampling signal of the output voltage Vo. The second comparator 710 receives the sampling signal of the output voltage Vo and compares it with the preset reference voltage. When the sampling signal of the output voltage Vo is not equal to the preset reference voltage, the second comparator 710 outputs the second processing signal. The interleaving controller 708 receives the second processing signal and outputs the first control signal to control the first high-voltage output module 704 and the second control signal to control the second high-voltage output module 705 according to the second processing signal. After adjusting, the output voltage Vo can reach a target value, and the first high-voltage module 704 and the second high-voltage output module 705 achieves interleaving conduction, so that the ripple of the output voltage can be reduced.

The second control unit 707 outputs the first control signal and the second control signal to interleaving control the first high-voltage output module 704 and second high-voltage output module 705. There is a phase difference between the first control signal and the second control signal, and preferably the phase difference is 180°. The first high-voltage output module and the second high-voltage output module are interleaving turn-on and turn-off, so that the ripple of the output voltage can be reduced greatly and the imaging precision and image quality of the X-ray apparatus can be improved.

The first high-voltage output module and the second high-voltage output module have independent input voltages. The control module 703 controls the power supply module 701 to adjust two independent power supply voltages Vbus1 and Vbus2 to make the first output voltage and the second output voltage opposite in polarity while substantially equal in value. The output power of the first high-voltage output module and the output power of the second high-voltage output module can maintain balance. In this way, it is convenient to choose the related components and parameters of the high voltage conversion module, the flexibility of the design can be improved and the service life of the X-ray apparatus can be extended.

Figure 8:
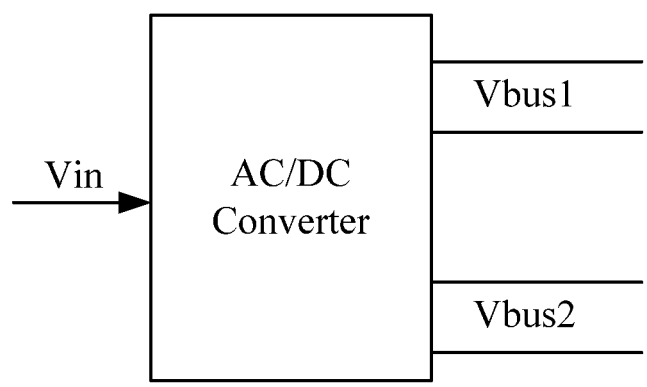
FIG. 8 is a circuit block diagram of the power supply module according to the second embodiment of the present disclosure.
Figure 9:
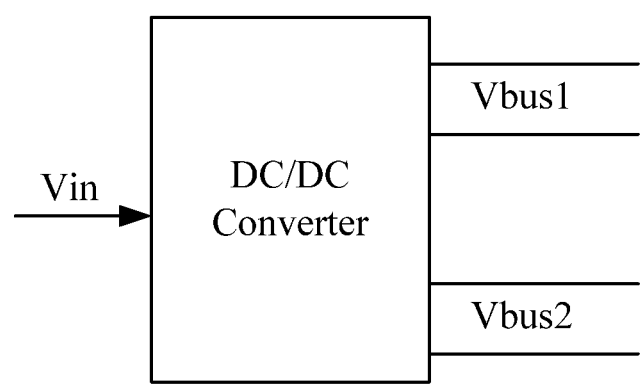
FIG. 9 is another circuit block diagram of the power supply module according to the second embodiment of the present disclosure.
Figure 11:
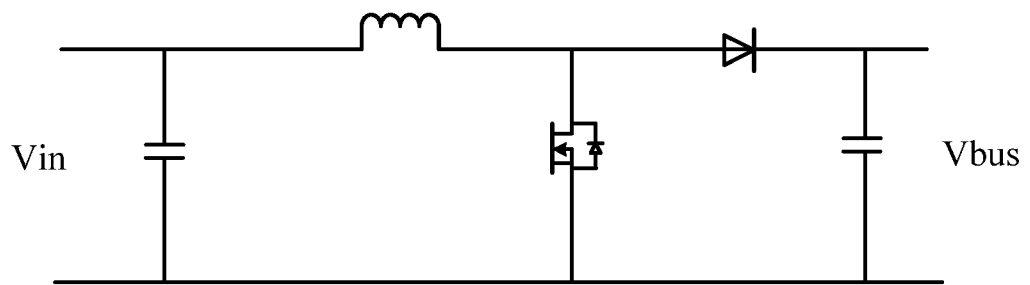
FIG. 11 is a circuit diagram of the DC/DC converter which is a boost circuit shown in FIG. 9.
Figure 12:
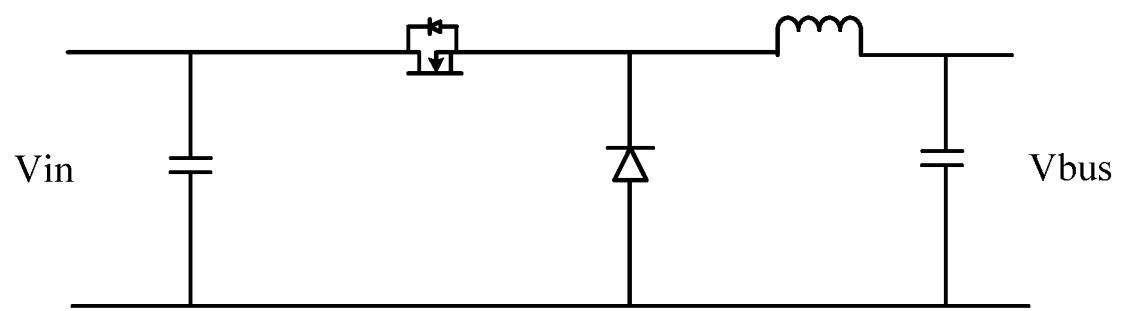
FIG. 12 is a circuit diagram of the DC/DC converter which is a buck circuit shown in FIG. 9.

FIG. 8 and FIG. 9 show the typical circuit diagrams of the power supply module shown in FIG. 6. In FIG. 8, the input voltage Vin is an AC voltage, the power supply module uses an AC/DC converter and outputs two power supply voltages Vbus1 and Vbus2 that are independent of each other. In FIG. 9, the input voltage Vin is a DC voltage, the power supply module uses a DC/DC converter and outputs two power supply voltages Vbus1 and Vbus2 that are independent of each other. FIG. 11 shows that the DC/DC converter shown in FIG. 9 is a boost circuit. FIG. 12 shows that the DC/DC converter shown in FIG. 9 is a buck circuit. It is noted that FIG. 11 and FIG. 12 only show two implements of the DC/DC converter, the actual application is not limited to this, and there is no need to illustrate all implements here. The first high-voltage output module 704 and second high-voltage output module 705 are both resonant circuits, such as the full-bridge series resonant DC/DC converter shown in FIG. 4. The resonant circuits can increase the switching frequency and reduce the voltage spike.

The controlling method of the high-voltage medical power supply device according to the present embodiment will be described as follows. The method includes the following steps. The power supply module 701 receives the voltage Vin inputted from the outside and obtains the first power supply voltage Vbus1 and the second power supply voltage Vbus2. The first high-voltage output module 704 and second high-voltage output module 705 respectively receive the first power supply voltage Vbus1 and the second power supply voltage Vbus2 and output the first output voltage +HV and the second output voltage −HV. And the control module 703 samples the first output voltage and the second output voltage and generates the power control signal, the first control signal and the second control signal according to the sampling results. The power control signal is used to control the power supply module 701, the first control signal and the second control signal are used to interleaving control the first high-voltage output module 704 and the second high-voltage output module 705. There is a phase difference between the first control signal and the second control signal, and preferably the phase difference is 180°, which can reduce the ripple of the output voltage greatly and improve the imaging precision and image quality of the X-ray apparatus.

Figure 10:
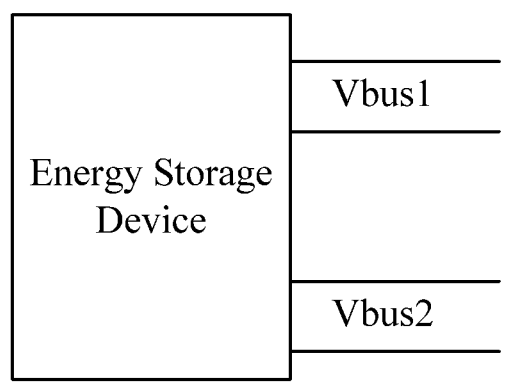
FIG. 10 is a circuit block diagram of the power supply module using energy storage device according to the second embodiment of the present disclosure.

It is important to note that the power supply module can also be realized by energy storages device or energy storages with DC/DC converters, which can supply power to the high-voltage medical power supply device when the input voltage is abnormal or can be used in a mobile type medical equipment without the input voltage. As illustrated in FIG. 10 the power supply module 701 uses the energy storage device such as batteries or capacitors to output the first power supply voltage Vbus1 and the second power supply Vbus2.

When the output power of the first high-voltage output module 704 is imbalance with the output power of the second high-voltage output module 705, the power supply module adjusts at least one of the Vbus1 and Vbus2 according to the power control signal, so that the output power of the first high-voltage output module 704 can be balanced with the output power of the second high-voltage output module 705. That is, the positive output voltage +HV is balanced with the negative output voltage −HV. For example, in case where the positive output voltage +HV is 60 kV and the negative output voltage −HV is −20 kV, the sampling signal of the positive output voltage +HV is not equal to that of the negative output voltage −HV. The first comparator 713 receives the sampling signals and compares the absolute values of the sampling signals. As the absolute value of the positive output voltage +HV is larger than that of the negative output voltage −HV, the first comparator 713 outputs a first processing signal. According to the first processing signal, the first controller 712 outputs the power control signal to control the power supply module. According to the power control signal, the power supply module reduces Vbus1 or increases Vbus2, or reduces Vbus1 while increases Vbus2, so that the output powers of the two high-voltage output modules can substantially keep balanced. Thus, the positive output voltage +HV is substantially balanced with the negative output voltage −HV. That is the absolute value of the positive output voltage +HV is approximately equal to that of the negative output voltage −HV. Similarly, if the absolute value of the positive output voltage +HV is smaller than that of the negative output voltage −HV, the adjusting method is opposite to that describe above and the redundant explanations of which are omitted here.

The summator 711 in the second control unit 707 receives the sampling signals of the positive output voltage +HV and the negative output voltage −HV and sums the absolute values of the two sampling signals to get the sampling signal of the output voltage Vo. The second comparator 710 receives the sampling signal of the output voltage Vo and compares it with the preset reference voltage. When the sampling signal of the output voltage Vo is not equal to the preset reference voltage, the second comparator 710 outputs a second processing signal to the interleaving controller 708. According to the second processing signal, the interleaving controller 708 outputs a first control signal to control the first high-voltage output module 704 and a second control signal to control the second high-voltage output module 705, so that the output voltage Vo can reach the target value. In this way, the first high-voltage output module 704 and the second high-voltage output module 705 are interleaving turn-on and turn-off, and the ripple of the output voltage Vo can be reduced.

Figure 7:
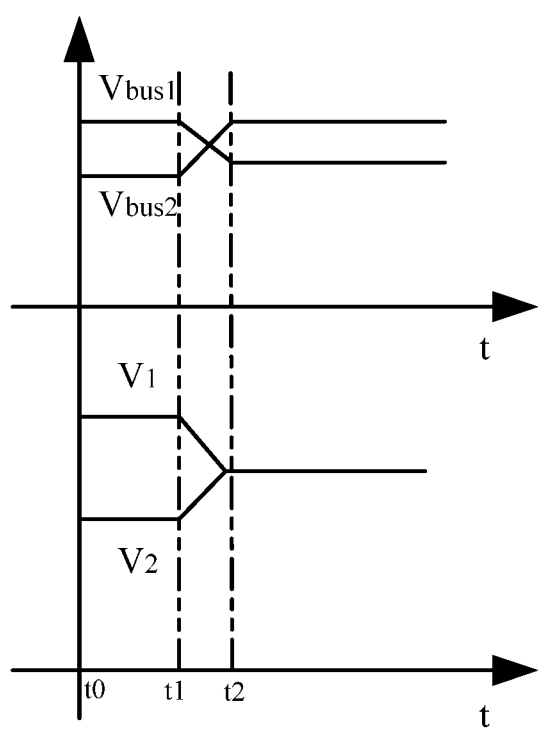
FIG. 7 is a schematic view showing the adjustments to the power voltage and the output voltage.

FIG. 7 is a schematic view showing the waveform adjustments of the power voltage and the output voltage. V1 and V2 in FIG. 7 respectively denote the absolute values of the sampled positive output voltage +HV and the negative output voltage −HV. As illustrated in FIG. 7, during the time $t_0 \sim t_1$, V1 is larger than V2, that is, the positive output voltage +HV is imbalance with the negative output voltage −HV. During the time $t_1 \sim t_2$, the power supply module adjusts Vbus1 and Vbus2 according to the power control signal so that the Vbus1 is reduced while the Vbus2 is increased until V1 is substantially equal to V2 at the time t2. When the absolute value of the positive output voltage +HV is substantially equal to that of the negative output voltage −HV, the adjustment is completed and the balance between the first output module and the second output module is attained.

FIG. 7 is just taken as an example. In practice, according to the sampling results, the Vbus1 can be increased or the Vbus2 can be reduced, or the process of increasing Vbus1 is performed simultaneously and coherently as the process of reducing Vbus 2 during the time $t_1 \sim t_2$. Similarly, when V1 is larger than V2, the Vbus1 can be reduced or the Vbus2 can be increased, or the process of reducing Vbus1 is performed simultaneously and coherently as the process of increasing Vbus 2, to adjust the V1 and V2 so that V1 is approximately equal to V2. The details are omitted here.

In present embodiment, the first high-voltage output module and the second high-voltage output module realize interleaving control via the first control signal and the second control signal, which can reduce the ripple of the high output voltage. And the power supply module 701 outputs two independent power supply voltages. The two independent power supply voltage are adjusted via the power control signal to make the positive output voltage +HV balance with the negative output voltage −HV. In this way, the damage to the high-voltage output module can be reduced and the flexibility of the design can be improved.

Figure 13:
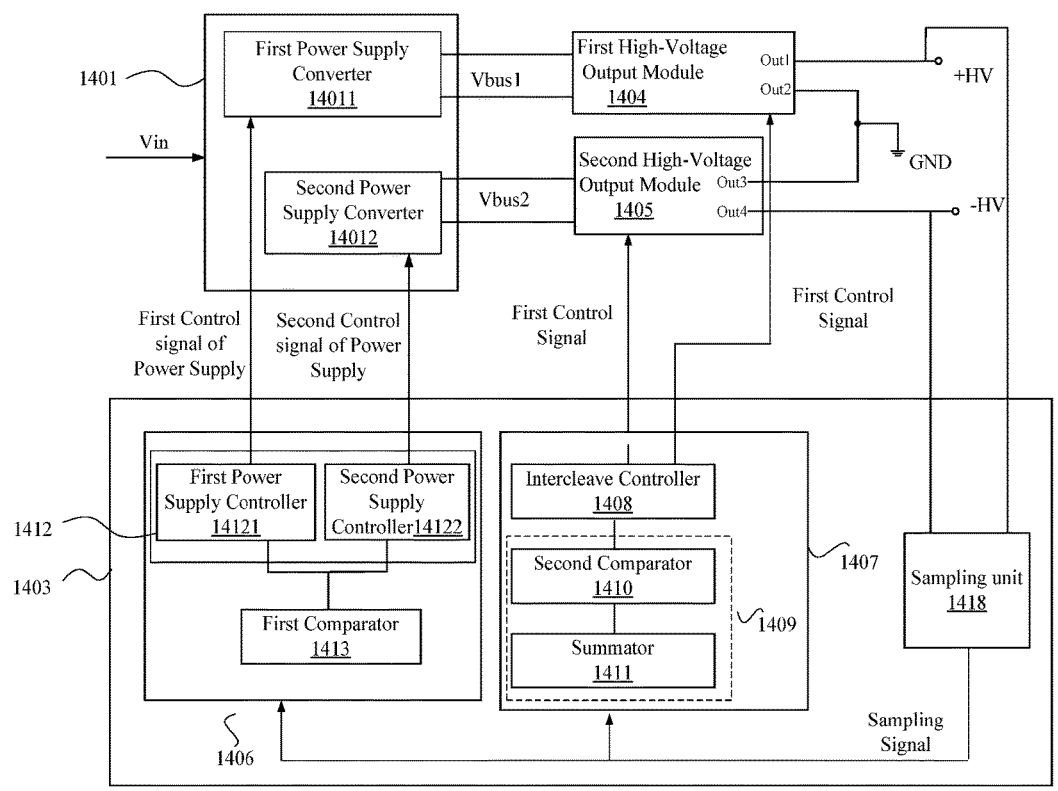
FIG. 13 shows a circuit diagram of the high-voltage medical power supply device according to the third embodiment of the present disclosure.

FIG. 13 shows the circuit diagram of the high-voltage medical power supply device according to the third embodiment of the present disclosure. Comparing with the second embodiment, the present embodiment further describes that the power supply module includes a first power supply converter and a second power supply converter that respectively output a first power supply voltage Vbus1 and a second power supply voltage Vbus2. As illustrated in FIG. 13, the power supply module 1401 includes a first power supply converter 14011 and a second power supply converter 14012 that respectively output two independent power supply voltages Vbus1 and Vbus2. The first high-voltage output module 1404 and second high-voltage output module 1405 are electrically connected to the output terminals of the power supply module 1401. Specifically, the first high-voltage output module 1404 is electrically connected to the output terminals of the power supply module 14011 to receive the power supply voltage Vbus1, and the second high-voltage output module 1405 is electrically connected to the output terminals of the power supply module 14012 to receive the power supply voltage Vbus2.

In present embodiment, the first high-voltage output module and the second high-voltage output module have separate power inputs. The first power supply converter 14011 converts the input voltage Vin to the first power supply voltage Vbus1 and inputs it to the first high-voltage output module. The second power supply converter 14012 converts the input voltage Vin to the second power supply voltage Vbus2 and inputs it to the second high-voltage output module.

Similar to the second embodiment, the control module 1403 includes the first control unit 1406, the second control unit 1407 and the sampling unit 1418. The sampling unit 1418 is connected with the first output terminal Out1 of the first high-voltage output module 1404 and the fourth output terminal Out4 of the second high-voltage output module 1405. The sampling unit 1418 samples the positive output voltage +HV and negative output voltage −HV, and output the sampling results to the first control unit 1406 and the second control unit 1407. omitted here.

The present embodiment differs from the second embodiment in that: the first control unit 1406 includes the first comparator 1413, the first power supply controller 14121 and the second power supply controller 14122. The first comparator 1413 is connected with the sampling unit to receive the positive output voltage +HV and the negative output voltage −HV obtained from sampling. The first comparator 1413 compares the absolute values of sampling results and outputs a first processing signal when the absolute values of the two sampling signals are not equal. Specially, if the absolute value of the sampled positive output voltage +HV is larger than that of the sampled negative output voltage −HV, the first comparator 1413 outputs a first processing signal. The first power supply controller 14121 outputs a first power control signal according to the first processing signal to control the first power supply converter 14011 to reduce the Vbus1. Or the second power supply controller 14122 outputs a second power control signal according to the first processing signal to control the second power supply converter 14012 to increase the Vbus2. Or according to the first processing signal, the first power supply controller 14121 and the second power supply controller 14122 respectively output a first power control signal and a second power control signal to control the first power supply converter to reduce the Vbus1 and the second power supply converter to increase the Vbus2. Similarly, if the absolute value of the positive output voltage +HV is less than that of the negative output voltage −HV, the first comparator 1413 outputs a first processing signal. According to the first processing signal, the first power supply controller 14121 outputs a first power control signal to control the first power supply converter 14011 to increase the Vbus1. Or according to the first processing signal, the second power supply controller 14122 outputs a second power control signal to control the second power supply converter 14012 to reduce the Vbus2. Or according to the first processing signal, the first power supply controller 14121 and the second power supply controller 14122 respectively output a first power control signal and a second power control signal to control the first power supply converter to increase the Vbus1 and the second power supply converter to reduce the Vbus2.

Figure 14:
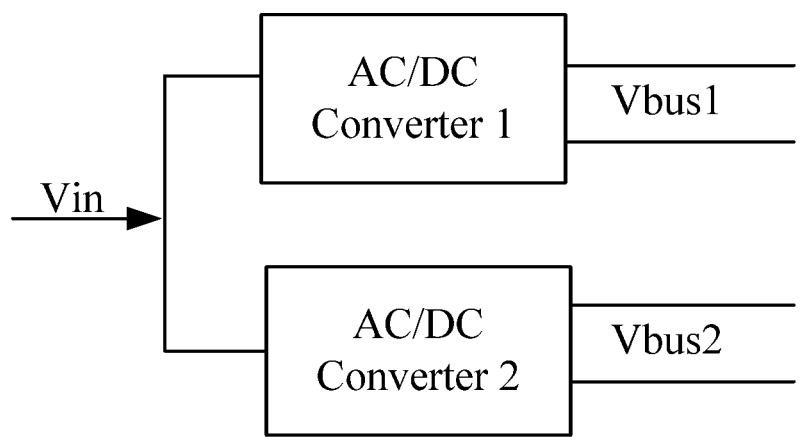
FIG. 14 is a circuit block diagram of the power supply module according to the third embodiment of the present disclosure.
Figure 15:
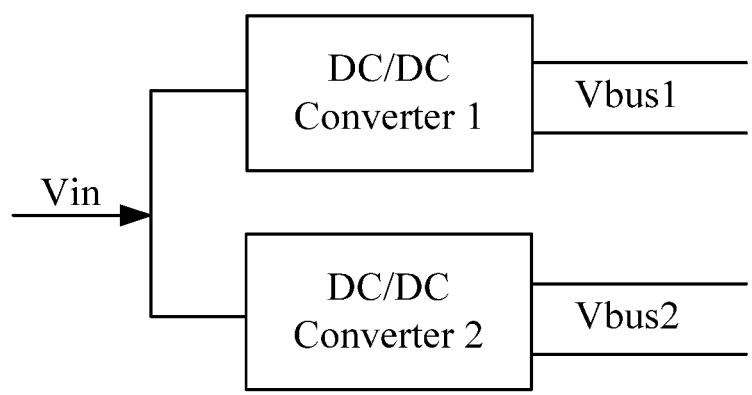
FIG. 15 is another circuit block diagram of the power supply module according to the third embodiment of the present disclosure.

The first power supply converter 14011 and the second power supply converter 14012 can be AC/DC converters or DC/DC converters, as illustrated in FIG. 14 and FIG. 15. FIG. 14 is a circuit block diagram of the power supply module in the present embodiment. When the input voltage Vin is an AC signal, the first power supply converter 14011 is corresponded to the AC/DC converter 1 in FIG. 14, and the second power supply converter 14012 is corresponded to the AC/DC converter 2 in FIG. 14. FIG. 15 is another circuit block diagram of the power supply module in the present embodiment. When the input voltage Vin is a DC signal, the first power supply converter 14011 is corresponded to the DC/DC converter 1 in FIG. 15, and the second power supply converter 14012 is corresponded to the DC/DC converter 2 in FIG. 15. The first high-voltage output module 1404 and second high-voltage output module 1405 both use resonant circuits such as the full-bridge series resonance DC/DC converter shown in FIG. 4, to increase the switching frequency and reduce the voltage spike, but it is not limited to this.

The controlling method of the high-voltage medical power supply device according to the present embodiment will be described as follows. The method includes the following steps. The first power supply converter module 14011 and the second power supply converter module 14012 both receive the voltage Vin inputted from the outside and respectively output the first power supply voltage Vbus1 and the second power supply voltage Vbus2. The first high-voltage output module 704 and second high-voltage output module 705 respectively receive the first power supply voltage Vbus1 and the second power supply voltage Vbus2 that are independent of each other and output the first output voltage and the second output voltage. Wherein the first output voltage is the positive output voltage +HV, and the second output voltage is the negative output voltage −HV. And the control module 1403 samples the positive output voltage and the negative output voltage and generates the first power control signal, the second power control signal, the first control signal, and the second control signal. The first power control signal is used to control the power supply module 14011, and the second power control signal is used to control the power supply module 14012. The first control signal and the second control signal are used to interleaving control the first high-voltage output module 1404 and the second high-voltage output module 1405. There is a phase difference between the first control signal and the second control signal, and preferably the phase difference is 180°. In this way, the ripple of the output voltage can be reduced greatly and the imaging precision and image quality of the X-ray apparatus can be improved.

The specific controlling process is similar to that of the second embodiment, and the redundant explanations are omitted.

Figure 16:
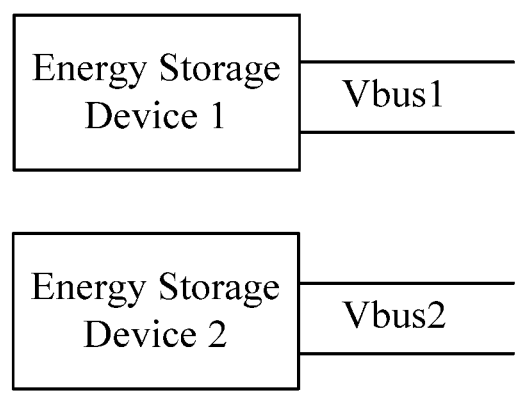
FIG. 16 is a circuit block diagram of the power supply module using energy storage device according to the third embodiment of the present disclosure.

It is important to note that the power supply module can also be realized by energy storage devices or energy storage devices with DC/DC converters, which can supply power to the high-voltage medical power supply device when the input voltage is abnormal or can be used in a portable medical equipment without the input voltage. As illustrated in FIG. 16, the first power supply converter 14011 uses the energy storage device 1 such as batteries or capacitors to output the first power supply voltage Vbus1, and the second power supply converter 14012 uses the energy storage device 2 such as batteries or capacitors to output the second power supply Vbus2.

In present embodiment, the power supply module includes a first power supply converter and a second power supply converter each of which outputs a separate power supply voltage. And the first power supply controller controls the first power supply converter and the second power supply controller controls the second power supply converter, so that the output voltage can be better controlled and the balance between the first output voltage and the second output voltage can be more precisely controlled and keep.

The terms "approximately" "substantially" used herein generally refer to a numeral error or scope within 10%, preferably within 5%. If it is not stated explicitly the referred numbers are all regarded as approximate values with for example the error or scope represented by the terms "approximately" "substantially" or other approximate values. It shall be noted that the above descriptions only illustrate preferred exemplary embodiments and technology principles of the present disclosure. One of ordinary skill in this art will appreciate that the present disclosure is not limited to the particular embodiments described herein. One of ordinary skill in this art may make various changes, re-adjustments and substitutions without departing from the protection scope of the present disclosure. Thus, although the present disclosure is described in detail with reference to the above embodiments, the present disclosure is not limited to these embodiments, and other equivalent embodiments may be included without departing from the concept of the present disclosure. The scope of the present disclosure is defined by the scope of the appended claims.

LIST OF REFERENCE SIGNS

304, 404, 704, 1404 first high-voltage output module
305, 405, 705, 1405 second high-voltage output module
301, 401, 701, 1401 power supply module
302 high voltage conversion module
303, 403, 703, 1403 control module
406, 706, 1406 first control unit
407, 707, 1407 second control unit
Out1 first output terminal
Out2 second output terminal
Out3 third output terminal
Out4 fourth output terminal
718, 1418 sampling unit
712, 1412 first controller
713, 1413 first comparator
408, 708, 1408 interleaving controller
409 second processing unit
710, 1410 second comparator
711, 1411 summator
14011 first power supply converter
14012 second power supply converter
14121 first power supply controller
14122 second power supply controller
R (+HV) corresponding ripple of the positive output voltage +HV
R (−HV) corresponding ripple of the negative output voltage −HV
R (Vo) corresponding ripple of the output voltage Vo
Vin input voltage
Vbus power supply voltage
Vbus1 first power supply voltage
Vbus2 second power supply voltage

What is claimed is:

1. A high-voltage medical power supply device, comprising:
a power supply module,
a high voltage conversion module, comprising a first high-voltage output module and a second high-voltage output module that are both electrically connected to an output terminal of the power supply module; and
a control module, electrically connected to an output terminal of the first high-voltage output module and an output terminal of the second high-voltage output module to respectively sample a first output voltage of the first high-voltage output module and a second output voltage of the second high-voltage output module,
and according to the first output voltage and the second output voltage obtained from sampling, the control module outputting a power control signal, a first control signal and a second control signal, respectively used to control the power supply module, the first high-voltage output module and the second high-voltage output module;
wherein there is a phase difference between the first control signal and the second control signal to interleaving control the first high-voltage output module and the second high-voltage output module.

2. The high-voltage medical power supply device according to claim 1, wherein the first high-voltage output module comprises a first output terminal and a second output terminal, and the second high-voltage output module comprises a third output terminal and a fourth output terminal,
the first output terminal and the fourth terminal are electrically connected with the control module, and the second output terminal is electrically connected with the third output terminal.

3. The high-voltage medical power supply device according to claim 2, wherein the first output voltage and the second output voltage are series connected with each other to generate a high output voltage,
and the first output voltage and the second output voltage are opposite in polarity and substantially equal in value.

4. The high-voltage medical power supply device according to claim 3, wherein the first high-voltage output module and the second high-voltage output module are resonant converters.

5. The high-voltage medical power supply device according to claim 1, wherein the power supply module is any one of AC/DC converters, DC/DC converters, energy storage devices and energy storage devices with DC/DC converters.

6. The high-voltage medical power supply device according to claim 5, wherein the power supply module outputs a power supply voltage to be an input of the first high-voltage output module and an input of the second high-voltage output module.

7. The high-voltage medical power supply device according to claim 5, wherein the power supply module outputs a first power supply voltage and a second power supply voltage that are independent of each other, and the first high-voltage output module is used to receive the first power supply voltage and the second high-voltage output module is used to receive the second power supply voltage.

8. The high-voltage medical power supply device according to claim 7, wherein the power supply module includes a first power supply converter and a second power supply converter, the first power supply converter outputs the first power supply voltage, the second power supply converter outputs the second power supply voltage.

9. The high-voltage medical power supply device according to claim 1, wherein the output terminals of the first high-voltage output module are coupled with the output terminals of the second high-voltage output module in series.

10. The high-voltage medical power supply device according to claim 1, wherein the control module comprises:
a first control unit, electrically connected with the power supply module to output the power control,
a second control unit, electrically connected with the first high-voltage output module and the second high-voltage output module to output the first control signal and the second control signal.

11. The high-voltage medical power supply device according to claim 10, wherein the control module further comprises a sampling unit used to sample the first high-voltage output voltage and the second high-voltage output voltage and correspondingly output sampled signals of the first output voltage and the second output voltage to the first control unit and the second control unit.

12. The high-voltage medical power supply device according to claim 11, wherein the first control unit comprises:
a first processing unit, electrically connected with the sampling unit and used to process the sampled signals of the first output voltage and the second output voltage and output a first processing signal;
a first controller, used to receive the first processing signal and output the power control signal to control the power supply module.

13. The high-voltage medical power supply device according to claim 12, wherein the power supply module includes a first power supply converter and a second power supply converter; and
the first controller comprises:
a first power controller, used to receive the first processing signal and output a first power control signal to control the first power supply converter,
a second power controller, used to receive the first processing signal and output a second power supply control signal to control the second power supply converter.

14. The high-voltage medical power supply device according to claim 11, wherein the second control unit comprises:
a second processing unit, electrically connected with the sampling unit and used to process the sampling signals of the first output voltage and the second output voltage and output a second processing signal;
a second controller, used to receive the second processing signal and output the first control signal and the second control signal.

15. A method of controlling a high-voltage medical power supply device, comprising:
a power supply module outputting a first power supply voltage and a second power supply voltage;
a first high-voltage output module and a second high-voltage output module of a high voltage conversion module respectively receiving the first power supply voltage and the second power supply voltage and correspondingly outputting a first output voltage and a second output voltage;
a control module sampling the first output voltage and the second output voltage, and generating a power control signal, a first control signal and a second control signal according to the first output voltage and the second output voltage; and
the first high-voltage output module receiving the first control signal, and the second high-voltage output module receiving the second control signal, wherein, there is a phase difference between the first control signal and the second control signal.

16. The method of a high-voltage medical power supply device according to claim 15, wherein a power input of the first high-voltage output module and a power input of the second high-voltage output module each are independent of each other.

17. The method of a high-voltage medical power supply device according to claim 15, wherein the power supply module receives the power control signal, and
when the first output voltage is imbalance with the second output voltage, the power supply module adjusts at least one of the first power supply voltage and the second power supply voltage according to the power control signal, and
the imbalance between the first output voltage and the second output voltage is eliminated.

18. The method of a high-voltage medical power supply device according to claim 15, wherein the first power supply voltage and the second power supply voltage are independent of each other.

19. The method of a high-voltage medical power supply device according to claim 15, wherein the output terminal of the first output module is coupled with the output terminal of the second output module in series.

* * * * *